(12) United States Patent
Hwang et al.

(10) Patent No.: US 11,313,831 B2
(45) Date of Patent: Apr. 26, 2022

(54) MICROELECTRODE BIOSENSOR USING DIELECTROPHORESIS

(71) Applicant: KOREA INSTITUTE OF SCIENCE AND TECHNOLOGY, Seoul (KR)

(72) Inventors: Kyoseon Hwang, Seoul (KR); Jinsik Kim, Seoul (KR); Hye Jin Kim, Seoul (KR); Yong Kyoung Yoo, Seoul (KR); Youngsoo Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 86 days.

(21) Appl. No.: 16/077,074

(22) PCT Filed: Nov. 9, 2016

(86) PCT No.: PCT/KR2016/012836
§ 371 (c)(1),
(2) Date: Aug. 10, 2018

(87) PCT Pub. No.: WO2017/142166
PCT Pub. Date: Aug. 24, 2017

(65) Prior Publication Data
US 2019/0041357 A1 Feb. 7, 2019

(30) Foreign Application Priority Data
Feb. 19, 2016 (KR) .................. 10-2016-0019479

(51) Int. Cl.
*B03C 5/00* (2006.01)
*G01N 33/543* (2006.01)
(Continued)

(52) U.S. Cl.
CPC ....... *G01N 27/44756* (2013.01); *B03C 5/005* (2013.01); *B03C 5/026* (2013.01);
(Continued)

(58) Field of Classification Search
CPC ......... G01N 33/54393; G01N 33/5438; G01N 27/44756; B03C 5/20; B03C 5/026; B03C 5/005; B03C 33/54393
See application file for complete search history.

(56) References Cited

U.S. PATENT DOCUMENTS 6,485,984 B1 * 11/2002 Kim ................. B82Y 15/00
435/7.4
8,641,881 B2 * 2/2014 Park ................. B03C 5/024
204/547
(Continued)

FOREIGN PATENT DOCUMENTS

KR          10-0777973 B1     11/2007
KR     10-2008-0016825 A      2/2008
(Continued)

OTHER PUBLICATIONS

KR-10-0777973 machine translation version (Year: 2007).*
(Continued)

*Primary Examiner* — Luan V Van
*Assistant Examiner* — Caitlyn Mingyun Sun
(74) *Attorney, Agent, or Firm* — Rabin & Berdo, P.C.

(57) ABSTRACT

An interdigitated electrode biosensor includes an insulating layer configured to fully cover a sensor forming region of a substrate, a first interdigitated microelectrode configured such that a plurality of first protruding electrodes is arranged in a shape of a comb on the substrate, a second interdigitated microelectrode configured such that a plurality of second protruding electrodes is arranged in a shape of a comb and each interdigitates with the plurality of first protruding electrodes, and a plurality of receptors that is immobilized in a space between the first interdigitated microelectrode and the second interdigitated microelectrode and reacts specifically to target biomaterials. Different voltages are uniformly or nonuniformly applied to the first interdigitated microelec- (Continued)

trode and the second interdigitated microelectrode to generate a dielectrophoretic force by a nonuniform electric field, improving the sensor by increasing the probability of specific reaction with the target biomaterials using the concentration effect through dielectrophoresis.

3 Claims, 14 Drawing Sheets

(51) Int. Cl.
  G01N 27/447 (2006.01)
  B03C 5/02 (2006.01)
(52) U.S. Cl.
  CPC ..... G01N 27/447 (2013.01); G01N 27/44704 (2013.01); G01N 33/5438 (2013.01); G01N 33/54393 (2013.01); B03C 2201/26 (2013.01)

(56) References Cited

U.S. PATENT DOCUMENTS

| | | | | |
|---|---|---|---|---|
| 9,079,189 | B2* | 7/2015 | Garcia | B03C 5/005 |
| 2009/0084686 | A1* | 4/2009 | Yun | G01N 33/5438 |
| | | | | 205/792 |
| 2010/0213056 | A1* | 8/2010 | Segawa | G01N 33/5438 |
| | | | | 204/403.01 |
| 2011/0024309 | A1* | 2/2011 | Lee | G01N 27/3276 |
| | | | | 205/792 |
| 2013/0264221 | A1 | 10/2013 | Kim et al. | |

FOREIGN PATENT DOCUMENTS

| | | |
|---|---|---|
| KR | 10-2009-0101764 A | 9/2009 |
| KR | 10-2010-0113698 A | 10/2010 |
| KR | 10-2012-0067967 A | 6/2012 |
| KR | 10-2015-0111246 A | 10/2015 |

OTHER PUBLICATIONS

L. Yang, Dielectrophoresis assisted immuno-capture and detection of foodborne pathogenic bacteria in biochips, Talanta 80 (2009) 551-558. (Year: 2009).*

Dielectrophoresis—Kylee Klinkowski (Year: 2021).*

C. Srisawat, Streptavidin aptamers: Affinity tags for the study of RNAs and ribonucleoproteins, RNA, 2001, 7: 632-641. (Year: 2001).*

* cited by examiner

MICROELECTRODE BIOSENSOR USING DIELECTROPHORESIS

TECHNICAL FIELD

The present disclosure relates to an interdigitated electrode biosensor, and more particularly, to an interdigitated electrode biosensor using dielectrophoresis in which receptors reacting specifically with target biomaterials are formed between interdigitated microelectrodes and the probability of specific reaction with the target biomaterials is increased using the concentration effect through dielectrophoresis, thereby improving the sensitivity and the detection width of the sensor.

BACKGROUND ART

Recently, many biosensors have been developed to detect the presence and concentration of various types of biomaterials including genes and proteins by electrical methods. One example is to use interdigitated microelectrodes. Because the area where receptors binding specifically to biomaterials are immobilized is substantially very wide in zigzag pattern, they are praised for their ability to properly measure even a low concentration of biomaterials.

Korean Patent No. 777973 (published on Nov. 29, 2007) teaches the use of interdigitated microelectrodes. However, in the case of the above patent, because the concentration is measured through an electric current flowing between the electrodes, there is inconvenience in having to use conductive particles separately to cause an electric current to flow between the electrodes.

In addition, in the case of the above patent, there is a problem that leakage of a larger amount of electric field that affects the impedance between the electrodes occurs above the electrodes than an amount of electric field generated between each electrode. In other words, changes in impedance are more affected by changes occurred above each electrode than reactions generated between each electrode, so the accuracy in impedance detection reduces and the impedance detection width and the detection limit is narrow and low, causing a problem with reliability and availability reduction.

RELATED LITERATURES

Patent Literatures

Korean Patent No. 777973 (published Nov. 29, 2007)

DISCLOSURE

Technical Problem

To solve the problem such as those described above, the present disclosure is directed to providing an interdigitated electrode biosensor using dielectrophoresis in which receptors reacting specifically with target biomaterials are formed between interdigitated microelectrodes, and the probability of specific reaction with the target biomaterials is increased using the concentration effect through dielectrophoresis, thereby improving the sensitivity and the detection width of the sensor.

Technical Solution

To achieve the above-described object, an interdigitated electrode biosensor using dielectrophoresis according to an embodiment of the present disclosure includes an insulating layer configured to fully cover a sensor forming region of a substrate, a first interdigitated microelectrode configured such that a plurality of first protruding electrodes is arranged in a shape of a comb on the substrate, a second interdigitated microelectrode configured such that a plurality of second protruding electrodes is arranged in a shape of a comb and each interdigitates with the plurality of first protruding electrodes formed in the first interdigitated microelectrode, and a plurality of receptors that is immobilized in a space between the first interdigitated microelectrode and the second interdigitated microelectrode and reacts specifically to target biomaterials, wherein different voltages are uniformly or nonuniformly applied to the first interdigitated microelectrode and the second interdigitated microelectrode to generate a dielectrophoretic force by a nonuniform electric field.

Advantageous Effects

According to the interdigitated electrode biosensor using dielectrophoresis in accordance with the present disclosure as described above, there are effects in increasing the impedance detection width a few ten to a few hundred times or more and improving the detection accuracy by forming receptors reacting specifically with target biomaterials on an insulator between each interdigitated microelectrode without using conductive particles to cause an electric current to flow between the electrodes.

Additionally, it is possible to improve the sensitivity and the detection width of the sensor by increasing the probability of specific reaction with target biomaterials using the concentration effect through dielectrophoresis.

BEST MODE

Hereinafter, the embodiments of the present disclosure will be described in detail with reference to the accompanying drawings.

Figure 1:
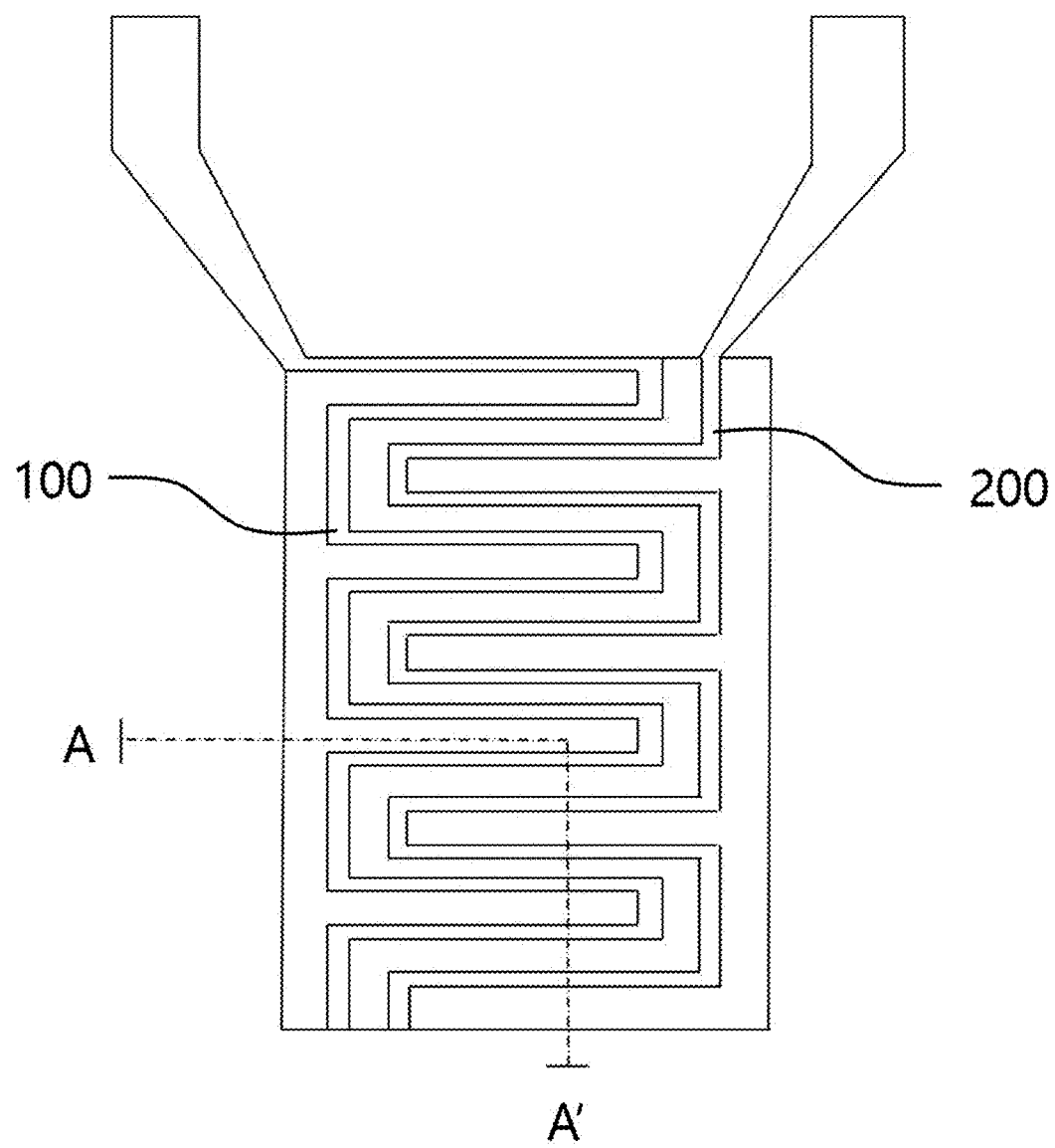
FIG. 1 is a diagram showing the configuration of an interdigitated electrode biosensor using dielectrophoresis according to an embodiment of the present disclosure.
Figure 2:
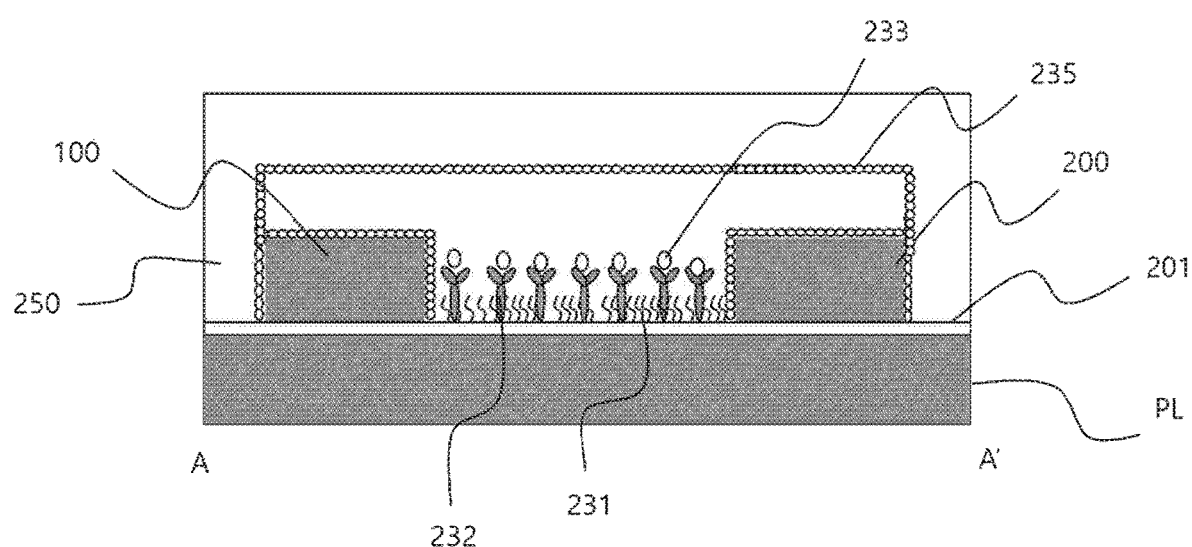
FIG. 2 is a detailed cross-sectional view taken along the line A-A' shown in FIG.

FIG. 1 is a diagram showing the configuration of an interdigitated electrode biosensor using dielectrophoresis according to an embodiment of the present disclosure, and FIG. 2 is a detailed cross-sectional view taken along the line A-A' shown in FIG. 1. Furthermore, FIG. 3 is a diagram showing the actual shape and detailed configuration of interdigitated microelectrodes shown in FIG. 2 when actually implemented.

Figure 3:
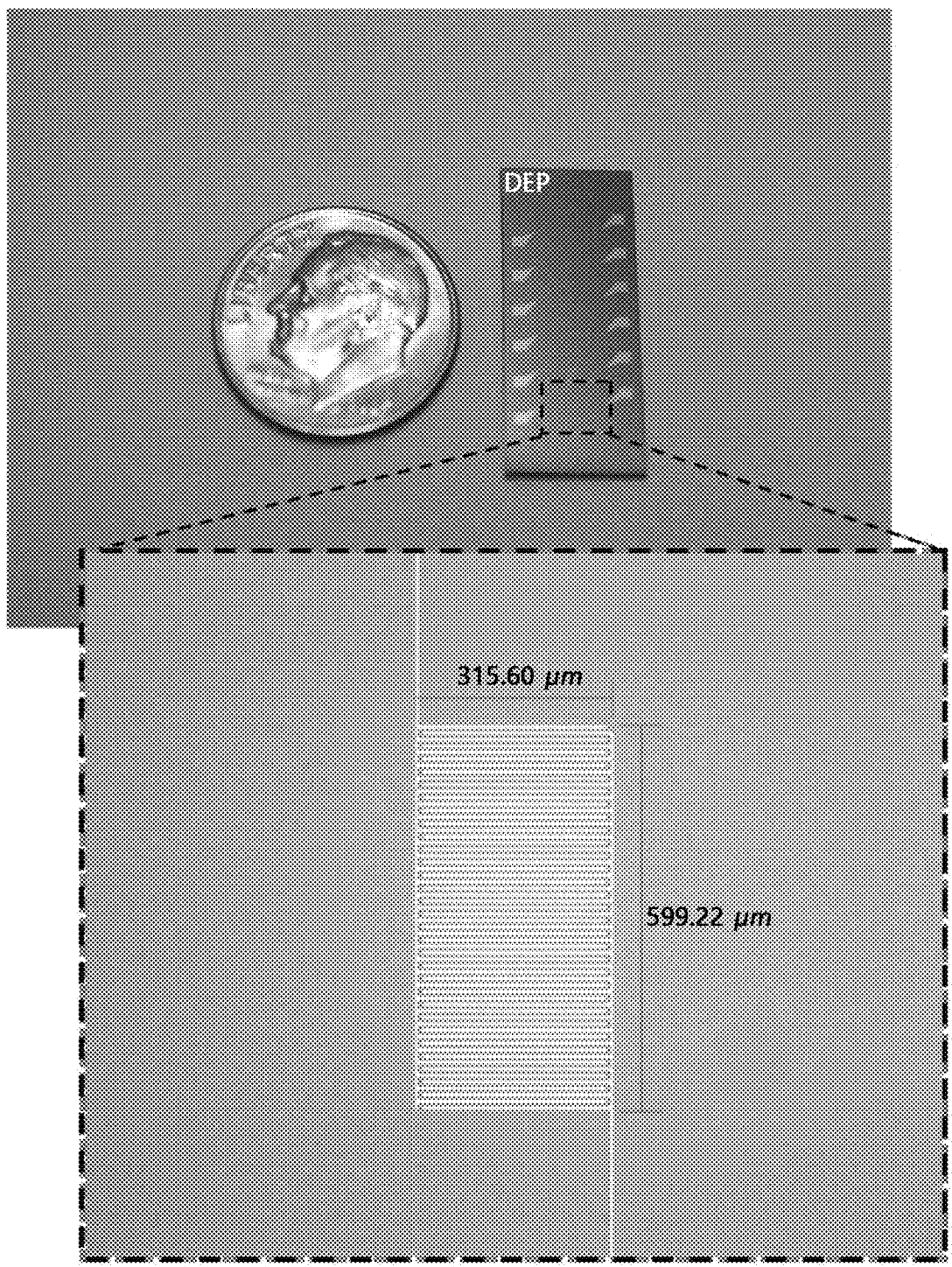
FIG. 3 is a diagram showing the actual shape and detailed configuration of interdigitated microelectrodes shown in FIG. 2 when actually implemented.

The interdigitated electrode biosensor shown in FIGS. 1 to 3 includes a first interdigitated microelectrode 100 configured such that a plurality of first protruding electrodes is arranged in the shape of a comb on a substrate PL, a second interdigitated microelectrode 200 configured such that a plurality of second protruding electrodes is arranged in the shape of a comb and each interdigitates with the plurality of first protruding electrodes formed in the first interdigitated microelectrode 100, and a plurality of receptors 232 that is immobilized in a space between the first interdigitated microelectrode 100 and the second interdigitated microelectrode 200 that interdigitate with each other and reacts specifically to target biomaterials 233, and different voltages are uniformly or nonuniformly applied to the first interdigitated microelectrode 100 and the second interdigitated microelectrode 200 to generate an dielectrophoretic force by a nonuniform electric field. Here, the plurality of receptors 232 may include at least one of beta-amyloid antibodies, aptamers and peptides.

First, describing the impedance detection characteristics by use of the interdigitated electrode biosensor using the reaction of the target biomaterials 233 as configured above, the impedance between the first interdigitated microelectrode 100 and the second interdigitated microelectrode 200 is summarized as follows:

$$Z = R + jX$$
$$= R + j(XL - XC)$$
$$= R - jXC$$
$$= R - j(1/wC)$$

Here, Z is impedance, R is resistance, X is reactance, C is capacitance, and w is angular frequency. The reactance X is divided into inductor component XL and capacitor component XC, and because the first interdigitated microelectrode 100 and the second interdigitated microelectrode 200 are not electrically connected to each other directly, it can be considered that the inductor component XL is neglected and only the capacitor component XC exists.

As shown in each of FIGS. 1 and 2, when the plurality of receptors 232 is immobilized and disposed in the space between the first interdigitated microelectrode 100 and the second interdigitated microelectrode 200, most of electric fields and impedance changes occur in horizontal direction in which the first interdigitated microelectrode 100 and the second interdigitated microelectrode 200 are disposed with the plurality of receptors 232 interposed between. By detecting variations in resistance and reactance, the quantity of the target biomaterials 233 can be accurately detected. Accordingly, the plurality of receptors 232 is immobilized in the space between the first interdigitated microelectrode 100 and the second interdigitated microelectrode 200, and quantitative analysis of the target biomaterials 233 is enabled by detecting changes in impedance at the space between the first interdigitated microelectrode 100 and the second interdigitated microelectrode 200, i.e., at the space between the first interdigitated microelectrode 100 and the second interdigitated microelectrode 200 facing each other, when the target biomaterials 233 reacts to the receptors 232.

Describing in detail, when the target biomaterials 233 or antibodies bind specifically to the plurality of receptors 232, the target biomaterials 233 are disposed between the first interdigitated microelectrode 100 and the second interdigitated microelectrode 200, and thus the resistance changes. Also, in the reactance, due to the properties of the target biomaterials, the value of capacitance C reduces and the XC value reduces. When the inductor component is neglected and only the reactance of the capacitor component is usually considered, it is easy to detect changes in impedance at high operating frequency, and in general, when the operating frequency is low, because changes in impedance are very small, it is difficult to detect the changes. Accordingly, to detect a very small amount of the target biomaterials 233, it is necessary to use high operating frequency.

However, if the frequency of the operating frequency is high, an electric current primarily flows through the route of the space above the specifically bound target biomaterials 233, and it fails to properly detect the target biomaterials 233. Furthermore, when the frequency is high, there is a risk that the target biomaterials 233 may not be properly detected due to damage caused by high frequency.

To detect the target biomaterials 233, it features using the low operating frequency of 10 Hz-100 Hz. Because the frequency is low, advantageously, it is possible to prevent the damage of the target biomaterials 233. Of course, in this case, because the frequency is low, a disadvantage is that it is difficult to detect a very small impedance change, but this disadvantage can be overcome by additionally using a differential amplifier.

In detecting biomaterials using the conventional interdigitated electrode sensor, antibodies are immobilized around each electrode including top and sides of the electrodes, and changes in impedance are observed at the time of binding to target molecules. In this case, antibodies are only immobilized in two dimensions on the surface of the electrodes. However, when the plurality of receptors 232 and antibodies are only formed and used between the first interdigitated microelectrode 100 and the second interdigitated microelectrode 200 according to an embodiment of the present disclosure, an amount of leaky electric field reduces, and the plurality of receptors 232 and antibodies are immobilized on regions on which an electric field concentrates, thereby increasing the accuracy and dynamic range of the sensor. Particularly, to detect the target biomaterials 233 using low operating frequency of 10 Hz-100 Hz as in the present disclosure, the spacing between the two electrodes 100, 200 is preferably 3-7 μm. The reason is because when the spacing is too small, for example, less than 3 μm, the deviation of the detected signal is too large to conduct a reliable test, and when the spacing is too large, for example, greater than 7 μm, sensitivity is too low to detect a small amount of biomaterials 233. When considering deviation and sensitivity, 5 μm is most preferable.

Figure 4A:
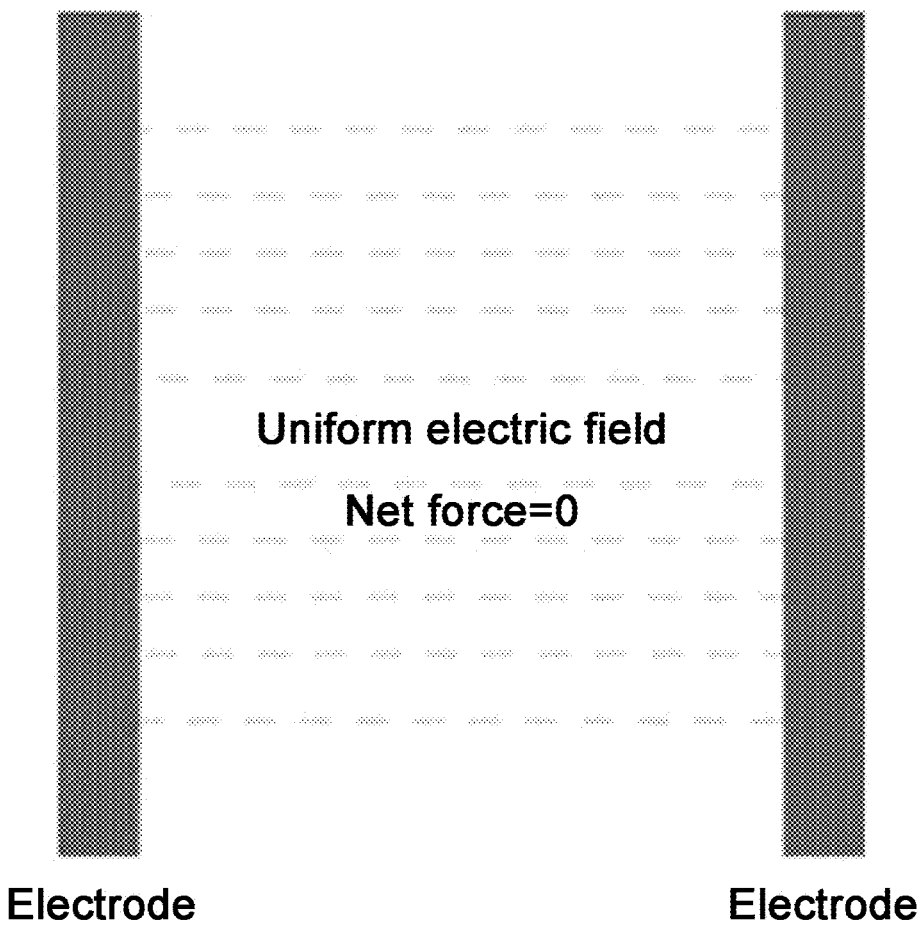
FIGS. 4a and 4b are diagrams showing a change in net force under the influence of dielectrophoresis.
Figure 4B:
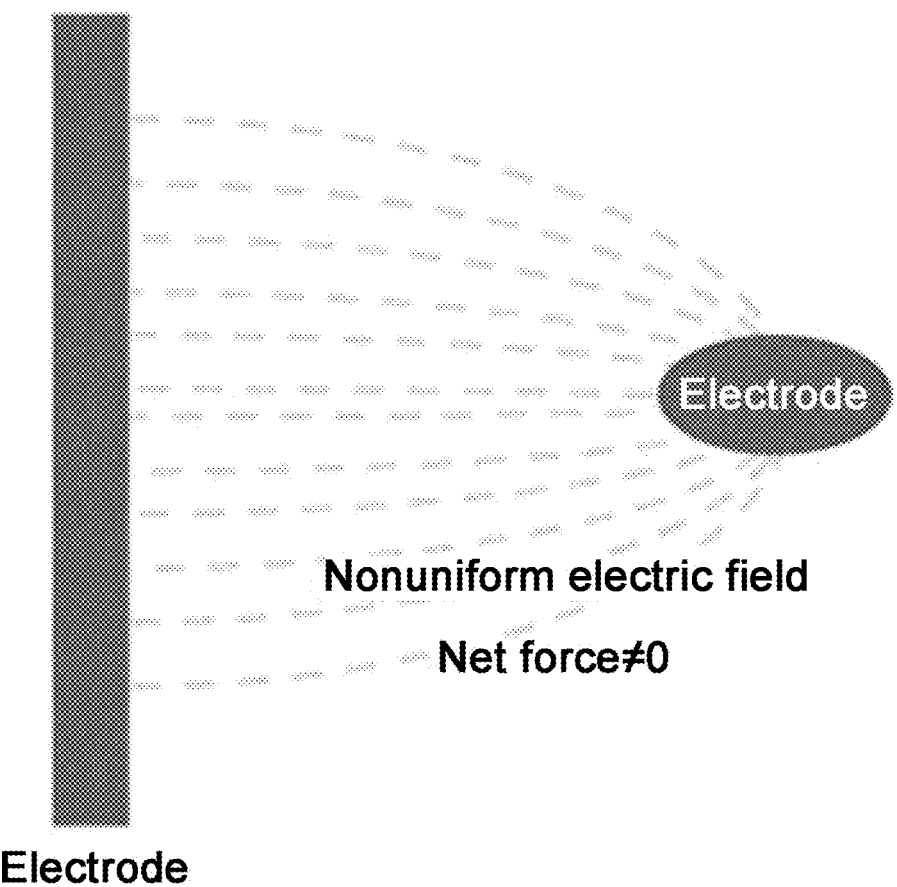
Figure 5A:
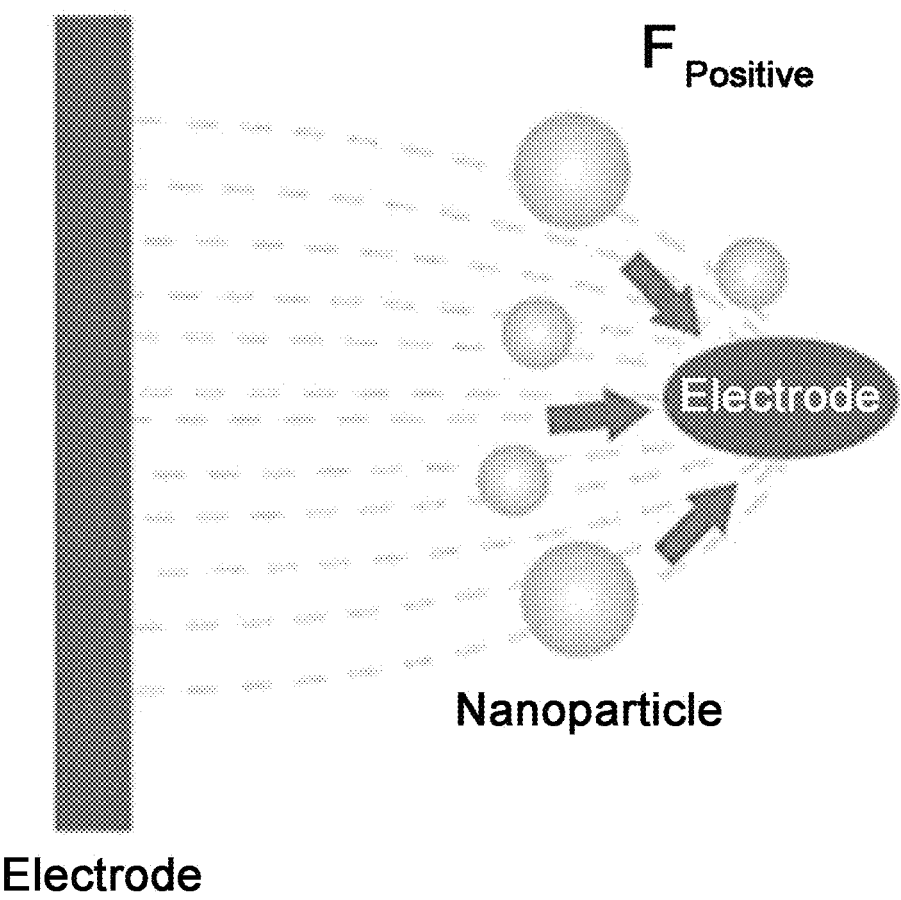
FIGS. 5a and 5b are diagrams showing the movement of particles under the influence of positive and negative electrophoresis.
Figure 5B:
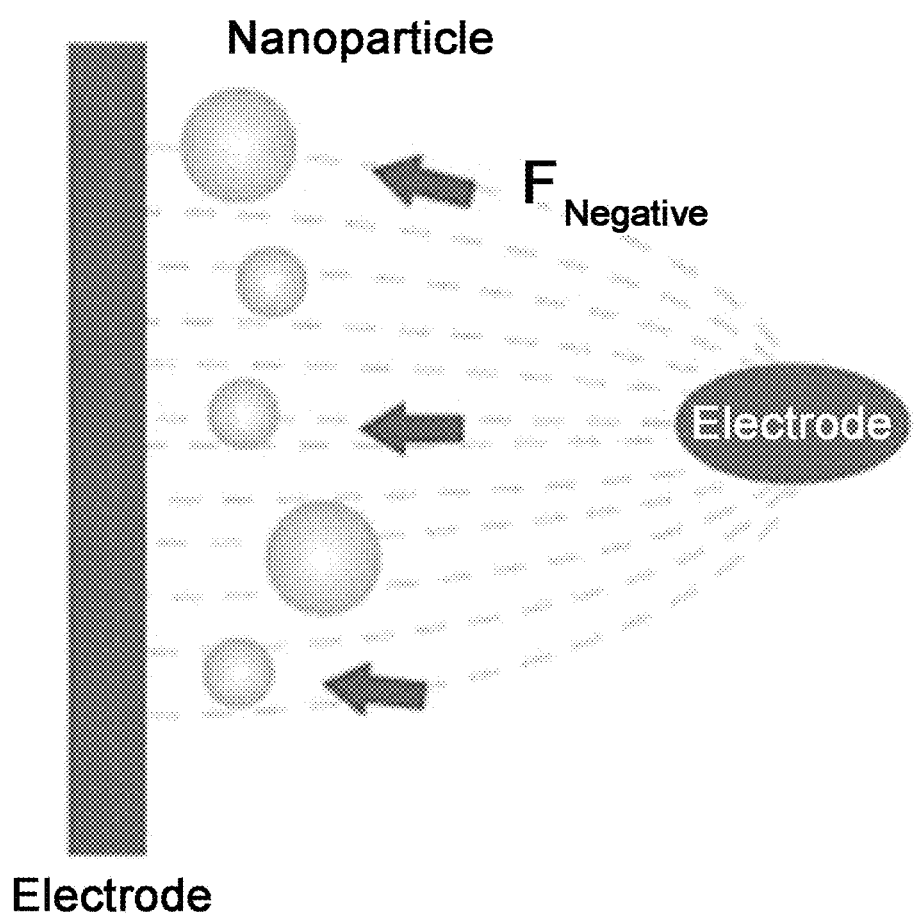

FIGS. 4a and 4b are diagrams showing a change in net force under the influence of dielectrophoresis. Furthermore, FIGS. 5a and 5b are diagrams showing the movement of particles under the influence of positive and negative electrophoresis.

First, referring to FIGS. 4a and 4b, dielectrophoretic forces that each exist by a uniform electric field and a nonuniform electric field are described as below. As opposed to a uniform electric field gradient as shown in FIG. 4(a), a force in a predetermined direction of a particular electrode exists within a nonuniform electric field of FIG. 4(b). Dielectrophoresis is defined as a phenomenon in which when a non-polar particle exists in a nonuniform alternating electric field, the dipole is induced to the particle, generating a net force within the electric field. The resulting net force may be defined as a dielectrophoretic force ($F_{DEF}$).

The magnitude and direction of dielectrophoresis induced to each particle that constitutes the target biomaterials 233 changes depending on the voltage and frequency of the applied electric field and the dielectric properties of the particle and medium, such as conductivity a and permittivity E. Accordingly, the force to which the particle of spherical shape is subjected by dielectrophoresis may be represented by the following Equation 1.

$$F_{DEP} = 2\pi\varepsilon_m r^3 \, Re[K(\omega)] \nabla |Ersm|^2 \qquad \text{[Equation 1]}$$

Here, $\varepsilon_m$ is the permittivity of the medium, r is the radius of the particle, $Re[k(\omega)]$ is the real part of the Clausius Mossotti factor, and Ersm denotes the root-mean square of the electric field. In this instance, a value of $k(\omega)$ is determined by the following Equation 2 according to the relative permittivity $\varepsilon^*_p$ of the particle and the relative permittivity $\varepsilon^*_m$ of the medium, and the polarity of the particle is determined by this value.

$$K(\omega) = \frac{\varepsilon^*_p - \varepsilon^*_m}{\varepsilon^*_p + 2\varepsilon^*_m} \qquad \text{[Equation 2]}$$

Together with this, referring to FIGS. 5a and 5b, when the $k(\omega)$ value is larger than 0, the force causes the particle to move toward a large electric field gradient. On the contrary, when the $k(\omega)$ value is smaller than 0, the force causes the particle to move toward a small electric field gradient according to the electric field formation type. These phenomena are also known as positive dielectrophoresis and negative dielectrophoresis respectively. Accordingly, when different voltages are uniformly or nonuniformly applied to generate a dielectrophoretic force by an electric field between the first interdigitated microelectrode 100 and the second interdigitated microelectrode 200 using dielectrophoresis, particles move toward a large or small electric field gradient according to the formation type formed between the first and second interdigitated microelectrodes 100, 200.

Figure 6A:
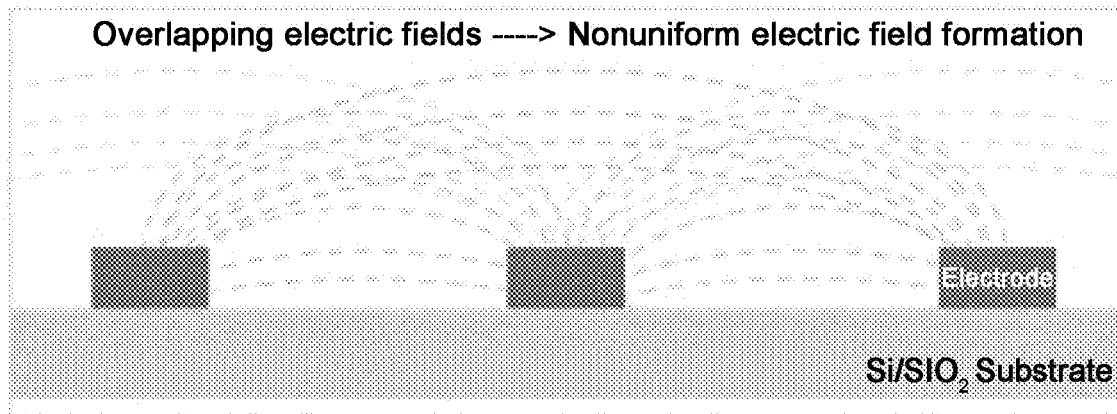
FIGS. 6a, 6b and 6c are diagrams showing the movement of particles under the influence of positive/negative electrophoresis of interdigitated microelectrodes shown in FIG. 1.
Figure 6B:
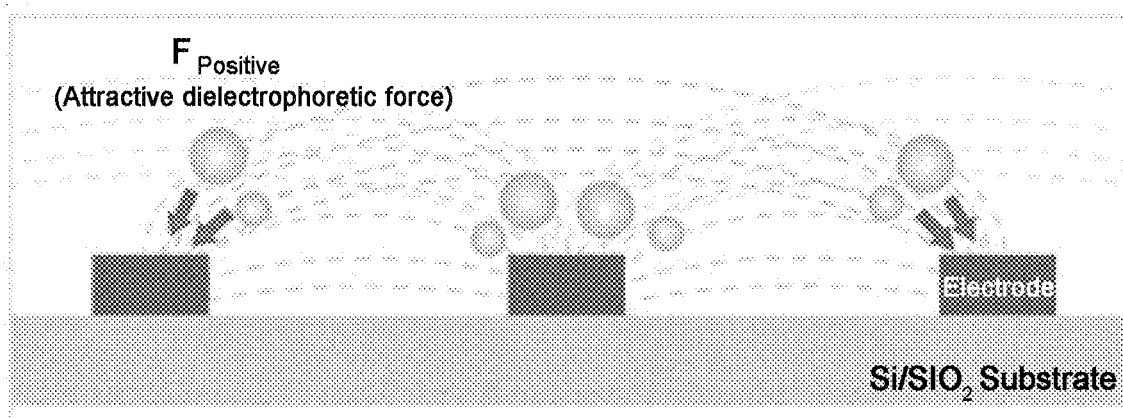
Figure 6C:
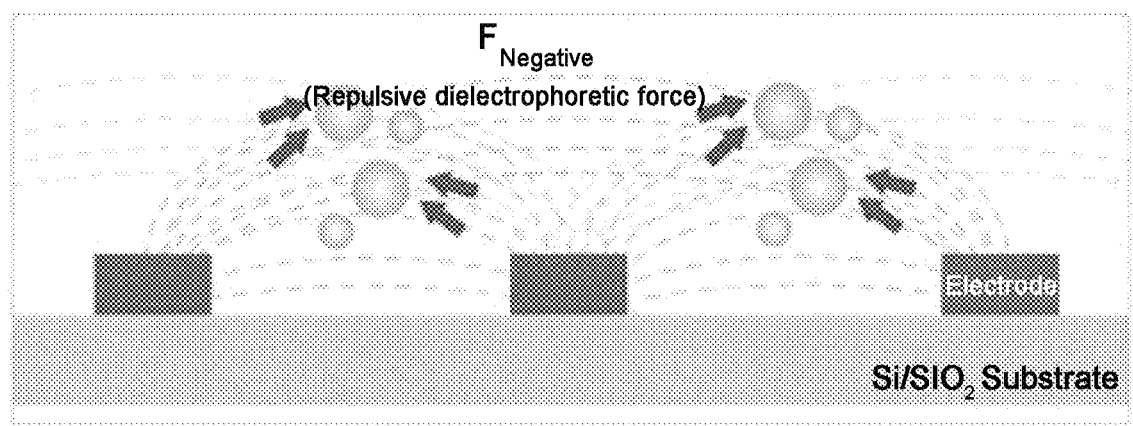

FIGS. 6a, 6b and 6c are diagrams showing the movement of particles under the influence of positive/negative electrophoresis of the interdigitated microelectrodes shown in FIG. 1.

As shown in FIGS. 6a, 6b and 6c, when uniform or nonuniform voltage is applied between the first interdigitated microelectrode 100 and the second interdigitated microelectrode 200, a nonuniform electric field is formed between the first and second interdigitated microelectrodes 100, 200 as shown in FIG. 6a, and this generates a dielectrophoretic force.

FIG. 6b shows a phenomenon in which particles move toward a large electric field gradient (electrode surface) according to the electric field formation type by a positive dielectrophoretic force generated within the interdigitated electrode sensor, and this is called focusing of particles.

On the contrary, FIG. 6c shows a phenomenon in which particles move toward a small electric field gradient (between electrodes) according to the electric field formation type by a negative dielectrophoretic force, and this is called trapping of particles.

As described above, when voltage is applied to each of the first and second interdigitated microelectrodes 100, 200 to generate negative dielectrophoresis according to the type and gradient of nonuniform electric field between the first and second interdigitated microelectrodes 100, 200, particles move and are concentrated by the dielectrophoretic force.

Particularly, when voltage applied to each of the first and second interdigitated microelectrodes 100, 200 is uniformly or nonuniformly applied by Equation 1 and Equation 2 within the range in which permittivity of the particles of the target biomaterials and the medium changes, a negative dielectrophoretic force is generated, and the target biomaterials move toward a small electric field gradient (between the electrodes) according to the electric field formation type by the negative dielectrophoretic force, and then the target biomaterials are concentrated and a reaction will occur.

As described above, to detect the moving biomaterials between the first interdigitated microelectrode 100 and the second interdigitated microelectrode 200, the receptors 232 reacting specifically (binding specifically) to the target biomaterials (target biomolecules) 233 are immobilized on the surface between the two electrodes, and quantitative analysis of the target biomaterials is enabled by detecting changes in impedance when the target biomaterials react to the receptors.

Figure 7:
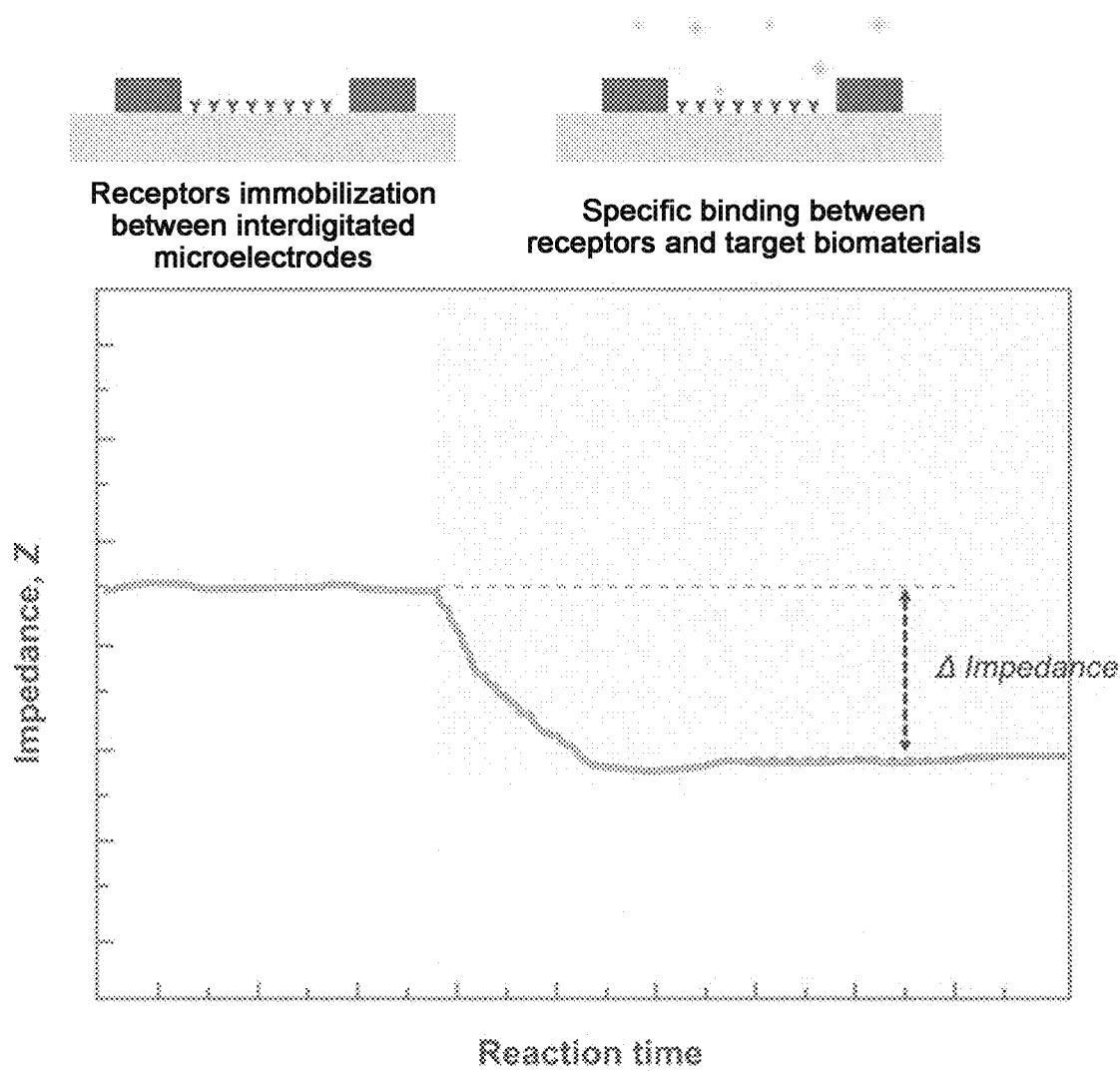
FIG. 7 is a graph showing a variation in impedance of the interdigitated electrode biosensor using dielectrophoresis shown in FIG. 1.

FIG. 7 is a graph showing a variation in impedance of the interdigitated electrode biosensor using dielectrophoresis shown in FIG. 1.

Referring to FIG. 7, upon binding of the target biomaterials 233 and the receptors 232, when voltage of different levels is applied to the first and second interdigitated microelectrodes 100, 200 to generate a negative dielectrophoretic force between the first and second interdigitated microelectrodes 100, 200, a trapping phenomenon of the target biomaterials 233 occurs, and due to the trapping phenomenon, concentration of the target biomaterials between the electrodes takes place, and the probability of specific reaction of the receptors 232 and the target biomaterials 233 increases. The increased probability of specific reaction produces effects in improving the sensitivity of the sensor and increasing the dynamic range area.

Figure 8A:
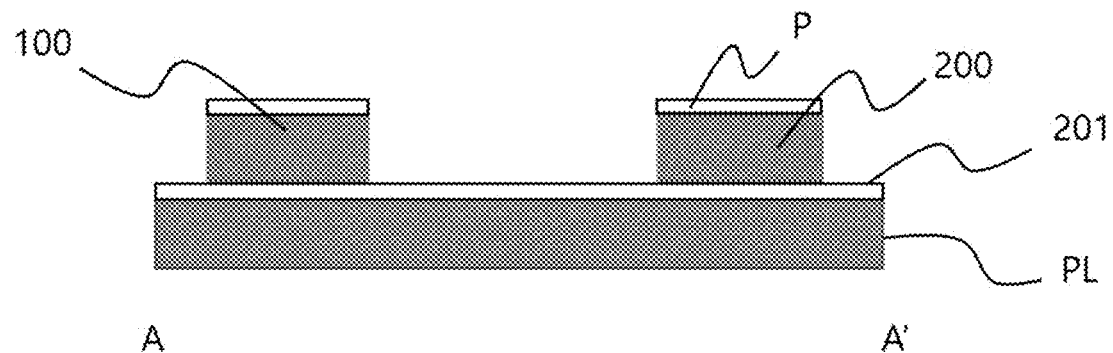
FIG. 8 is a cross-sectional view illustrating a method for fabricating the interdigitated electrode biosensor shown in FIGS. 1 to 3.
Figure 8B:
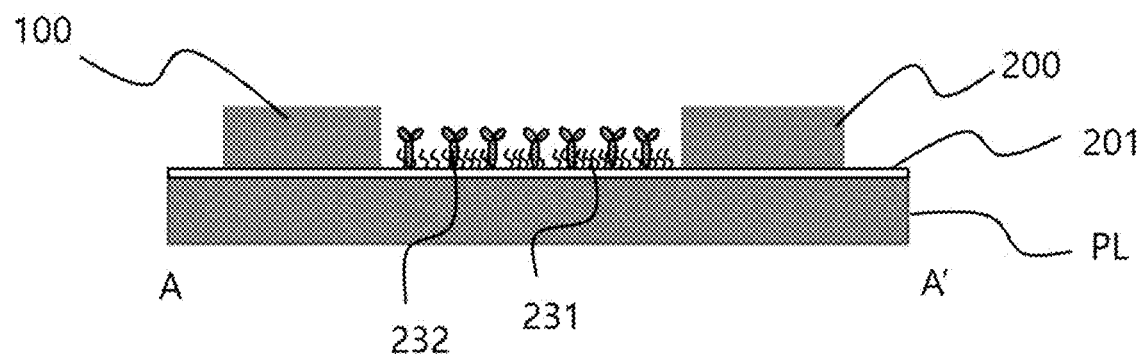
Figure 8C:
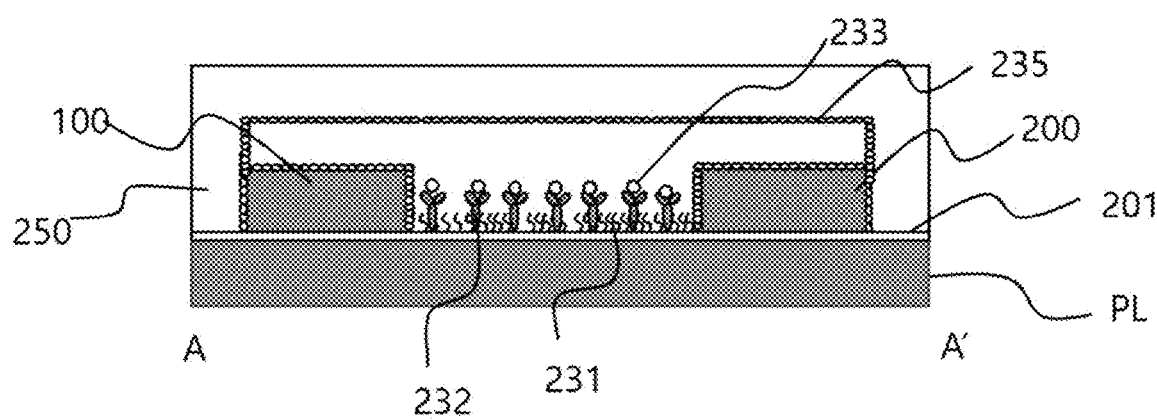

FIGS. 8a, 8b and 8c are cross-sectional views illustrating a method for fabricating the interdigitated electrode biosensor shown in FIGS. 1 to 3.

As shown in FIG. 8a, to form an insulating layer 201, a 500 nm thick silicon dioxide layer $SiO_2$ is formed on a substrate PL by thermal oxidation, and a metal layer is formed by deposition of titanium (Ti) of any one of 30 to 50 nm in thickness and platinum (Pt) of any one of 150 to 200 nm in thickness on the silicon dioxide layer by a sputtering method. The titanium (Ti) layer is used as an adhesion layer for increasing the bond strength of the platinum (Pt) layer and the silicon dioxide layer. The substrate on which $Si/SiO_2/Ti/Pt$ are deposited in that order goes through photoresist micropatterning by a photolithography process.

Subsequently, the photoresist micropatterned multilayer thin film deposited wafer goes through etching of the titanium (Ti) layer and the platinum (Pt) layer in a sequent order using Inductively Coupled Plasma Reactive Ion Etcher (ICP-RIE) to form two electrodes 100, 200 in metal patterns, followed by removal of the photoresist film pattern.

(B) Subsequently, a surface treatment process is performed, and in the surface treatment step, a Calixcrown Self-Assembled Monolayer (SAM) or a polyvinylpyrrolidone (PVP) surface modified material layer is formed as a liking molecule layer 231 on the surface of the insulating layer 201 between the first interdigitated microelectrode 100 and the second interdigitated microelectrode 200 to selectively immobilize beta-amyloid antibodies. Additionally, beta-amyloid antibodies as the receptors 232 are immobilized on the linking molecule layer 231. Thus, the target biomaterials 233 or beta-amyloid may selectively specifically bind to the receptors 232.

Here, a reference electrode for signal comparison of a beta-amyloid antibody immobilized interdigitated electrode sensor and a prostate-specific antigen (PSA) antibody immobilized interdigitated electrode sensor for selectivity detection (negative control) are each constructed.

Subsequently, if a region to which the target biomaterials 233 specifically bind is completely exposed to the outside, a detection error may occur, so it is necessary to cover this region. To this end, it is desirable that a protective cap 250 is formed on the first interdigitated microelectrode 100 and the second interdigitated microelectrode 200. Moreover, to prevent the non-specific binding of any material other than beta-amyloid, a polydimethylsiloxane (PDMS) chip having two microchannels may be attached, and an adsorption blocking layer (Bovine Serum Albumin) 235 may be coated on a region except the microchannels and the antibody immobilized region of the interdigitated electrode sensor, i.e., an inner wall of the protective cap 250 except a region where the receptors 232 are not immobilized, and the surface of the first interdigitated microelectrode 100 and the second interdigitated microelectrode 200.

In addition, for a stabilization operation, preferably a stabilization operation is performed by injecting 0.1×PBS into all the two channels, and observing signals until the point in time in which impedance signals of the interdigitated electrode sensor are stably uniformly maintained. The sensor having undergone the stabilization operation has the initial stabilization time for 5 minutes, and then 10 pg/mL of beta-amyloid is injected into the channels and variations of impedance signals are observed for about 15 minutes to detect the antigen-antibody reaction of beta-amyloid. Subsequently, to minimize the non-specific binding or the influence of electrical signals by the biomaterials present in the PBS solution, a clear PBS solution is injected to cause a solution change. Additionally, the size of the final signal by specific reaction of beta-amyloid and antibodies can be detected by observing variations in impedance for 5 minutes.

Figure 9:
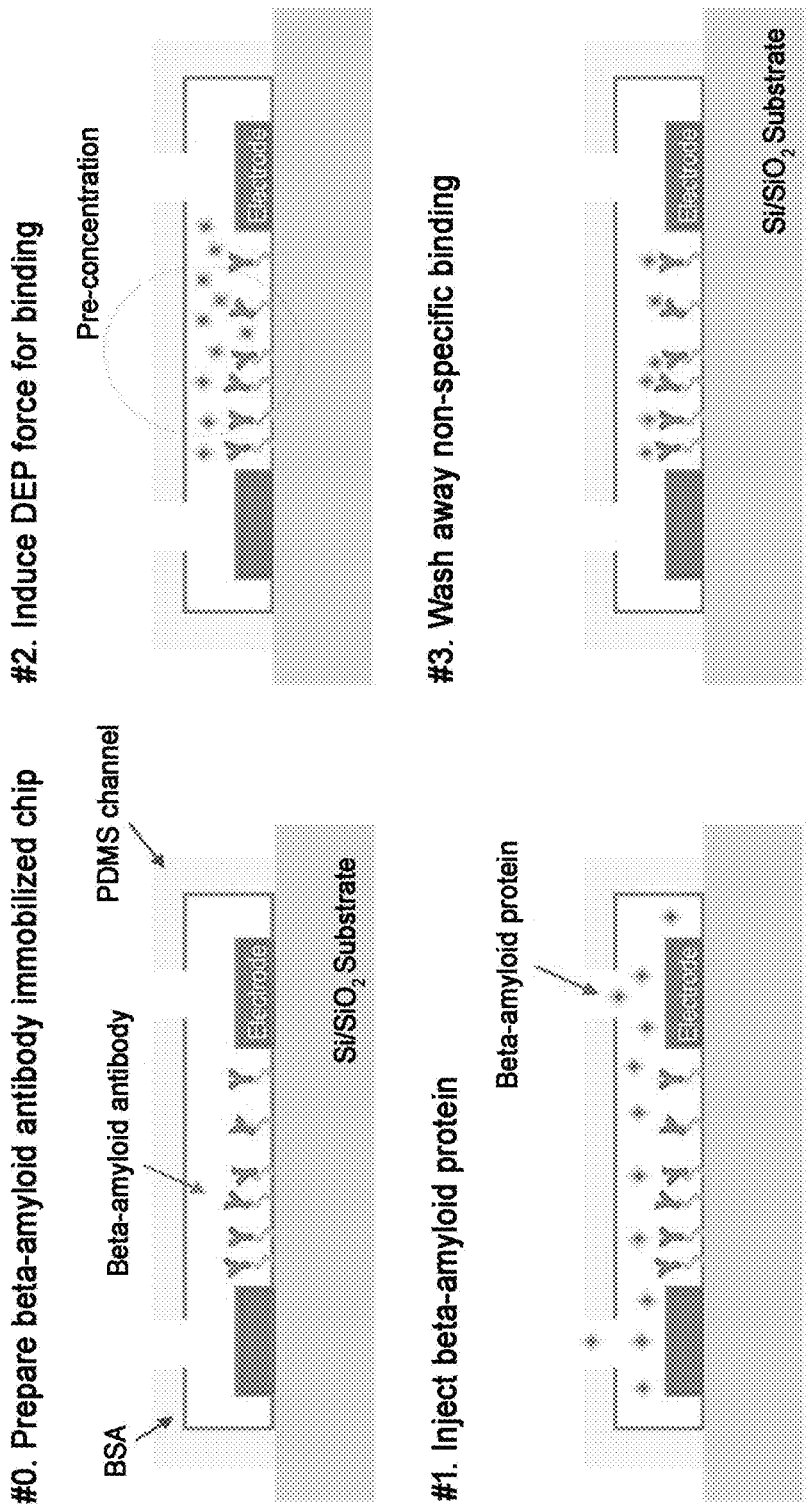
FIG. 9 is a diagram illustrating a method for concentration of target biomaterials between interdigitated microelectrodes using dielectrophoresis.

FIG. 9 is a diagram illustrating a method for concentration of the target biomaterials between the interdigitated microelectrodes using dielectrophoresis.

Referring to FIG. 9, after preparing an interdigitated electrode biosensor in which at least one material of beta-amyloid antibodies, aptamers and peptides is immobilized on the receptors 232, beta-amyloid is injected into microchannels of the interdigitated electrode biosensor.

Subsequently, when voltage applied to each of the first and second interdigitated microelectrodes 100, 200 is uniformly or nonuniformly applied by Equation 1 and Equation 2 within the range in which permittivity of the particles of the target biomaterials and the medium changes, a negative dielectrophoretic force is generated, and the target biomaterials move toward a small electric field gradient (between electrodes) according to the electric field formation type by the negative dielectrophoretic force, and then the target biomaterials are concentrated and a reaction will occur. When binding is finished, the applied alternating electric field is removed and impedance changes occurred by specific binding are measured.

Figure 10:
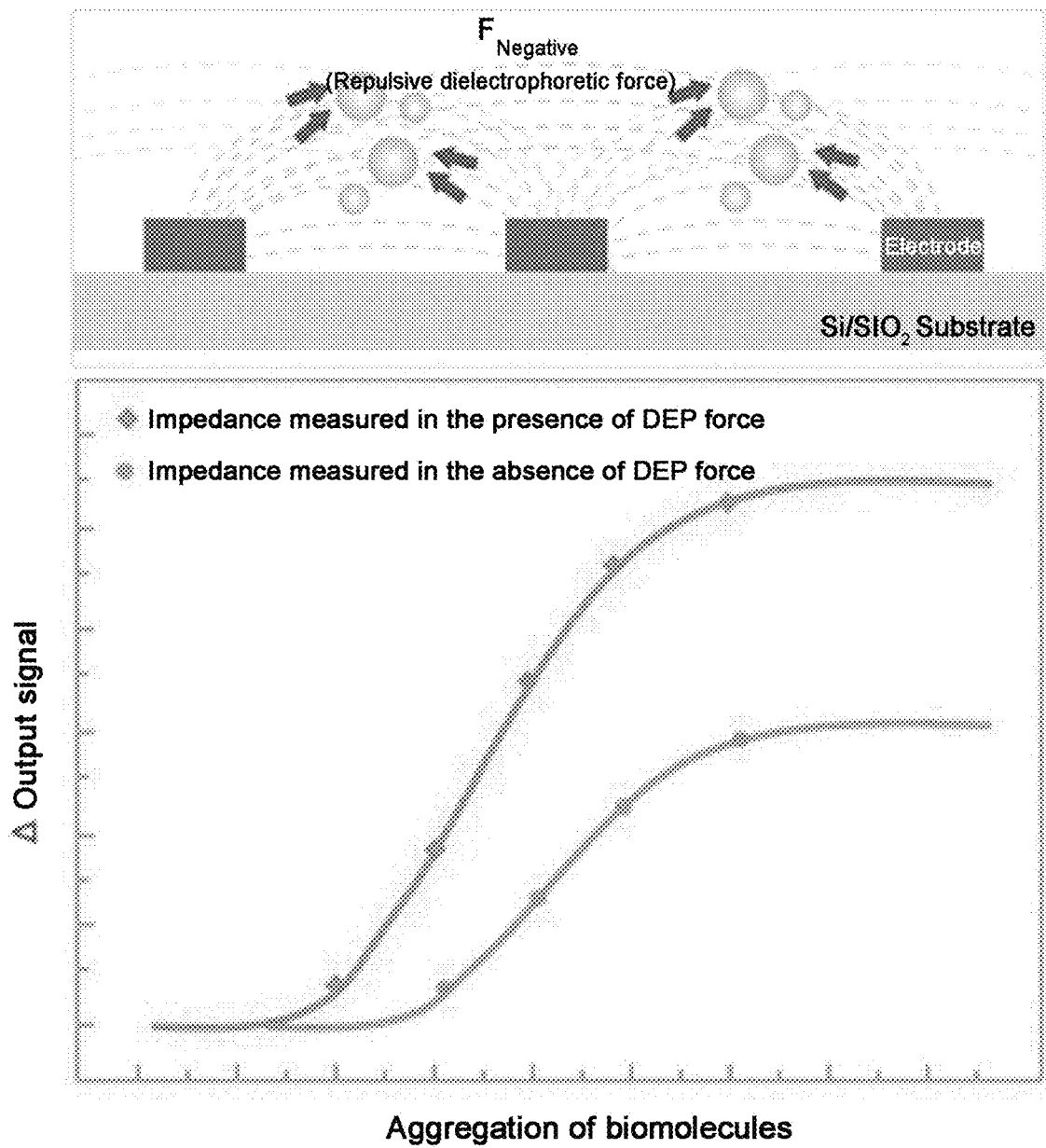
FIG. 10 is a graph showing changes in sensitivity and detection width of an interdigitated electrode biosensor using dielectrophoresis.

FIG. 10 is a graph showing changes in sensitivity and detection width of the interdigitated electrode biosensor using dielectrophoresis.

As shown in FIG. 10, as opposed to the conventional interdigitated electrode sensor, in the interdigitated electrode biosensor using dielectrophoresis according to the present disclosure, upon binding of the target biomaterials 233 and the receptors 232, when voltage of different levels is applied to the first and second interdigitated microelectrodes 100, 200 to generate a negative dielectrophoretic force between the first and second interdigitated microelectrodes 100, 200, a trapping phenomenon of the target biomaterials 233 or beta-amyloid occurs, and due to the trapping phenomenon, beta-amyloid is concentrated between the electrodes and specific binding of the concentrated beta-amyloid and the beta-amyloid antibodies takes place.

Accordingly, the probability of specific reaction of the receptors 232 and the target biomaterials 233 increases, and the increased probability of specific reaction leads to the sensitivity improvement and dynamic range area increase effects of the sensor.

Figure 11:
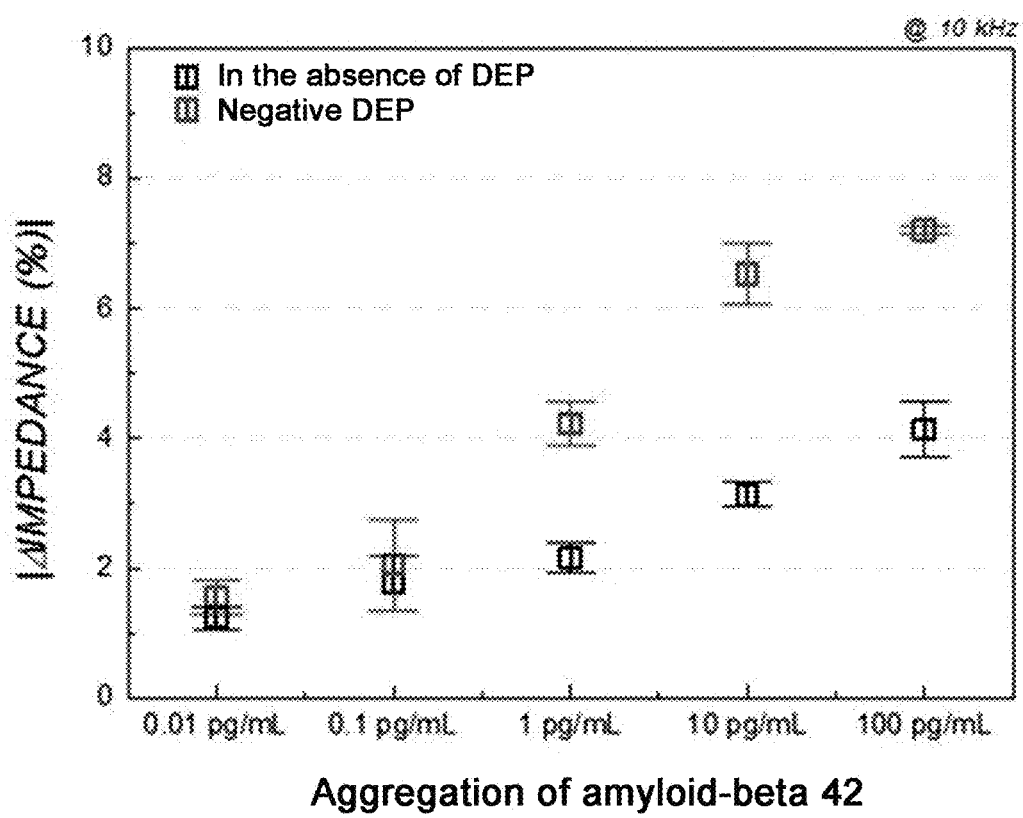
FIG. 11 is a graph showing comparison results of sensitivity between an interdigitated electrode biosensor using dielectrophoresis according to the present disclosure and a conventional biosensor.

FIG. 11 is a graph showing comparison results of sensitivity between the interdigitated electrode biosensor using dielectrophoresis according to the present disclosure and the conventional biosensor.

As shown in FIG. 11, a negative dielectrophoretic force is applied to the interdigitated electrode biosensor of the present disclosure to induce the concentration of the target biomaterials 233 or beta-amyloid when the target biomaterials 233 or beta-amyloid react with the receptors 232. The concentration of beta-amyloid increases the probability of specific binding between the receptors 232 and beta-amyloid and enhances the sensitivity of the sensor. This effect can be seen from the beta-amyloid detection experiment, and it can be seen that when beta-amyloid with concentrations of 0.01 pg/mL to 100 pg/mL is injected into the sensor, the interdigitated electrode biosensor to which the negative dielectrophoretic force is applied as indicated by the red squares of FIG. 11 has improvement over the conventional biosensor in black.

According to the interdigitated electrode biosensor using dielectrophoresis in accordance with the present disclosure as described above, it is possible to increase the impedance detection width a few ten to a few hundred times or more and improve the detection accuracy by forming receptors reacting specifically with target biomaterials on an insulator between each interdigitated microelectrode without using conductive particles to cause an electric current to flow between the electrodes. Additionally, it is possible to improve the sensitivity and the detection width of the sensor by increasing the probability of specific reaction with target biomaterials using the concentration effect through dielectrophoresis.

While the embodiments of the present disclosure have been hereinabove described, those having ordinary skill in the corresponding technical field will understand that various modifications and changes may be made thereto without departing from the spirit and scope of the present disclosure set forth in the appended claims.

What is claimed is:

1. An interdigitated electrode biosensor using dielectrophoresis, comprising:
   an insulating layer configured to fully cover a sensor forming region of a substrate;
   a first interdigitated microelectrode configured such that a plurality of first protruding electrodes is arranged in a shape of a comb on the substrate;
   a second interdigitated microelectrode configured such that a plurality of second protruding electrodes is arranged in a shape of a comb and each interdigitates with the plurality of first protruding electrodes formed in the first interdigitated microelectrode;
   a plurality of receptors that is immobilized in a space between the first interdigitated microelectrode and the second interdigitated microelectrode and reacts specifically to target biomaterials, and
   at least one voltage source configured to apply voltages at different levels,
   wherein
   the first interdigitated microelectrode and the second interdigitated microelectrode are configured to, in response to the voltages applied at the different levels,
   generate a dielectrophoretic force by a nonuniform electric field between the first interdigitated microelectrode and the second interdigitated microelectrode,
   generate a negative dielectrophoretic force within a range in which conductivity and permittivity of particles of the target biomaterials and a medium change, and
   form a smaller gradient region of the nonuniform electric field, compared to a gradient of another region of the nonuniform electric field, according to an electric field formation type by the negative dielectrophoretic force,
   the smaller gradient region being positioned between the first and second interdigitated microelectrodes, and
   the smaller gradient region being configured to cause concentration of the target biomaterials by movement of the target biomaterials toward the smaller gradient region;
   wherein the different voltages applied to each of the first interdigitated microelectrode and the second interdigitated microelectrode are uniformly or nonuniformly applied by the following Equation 1 and Equation 2 within a range in which permittivity of particles of the target biomaterials and a medium changes:

$$F_{DEP} = 2\pi \varepsilon_m r^3 \, \mathrm{Re}[K(\omega)] \nabla |Ersm|^2 \qquad \text{[Equation 1]}$$

where $\varepsilon_m$ is permittivity of the medium, r is radius of a particle, $\mathrm{Re}[k(\omega)]$ is a real part of a Clausius Mossotti factor, and Ersm denotes a root-mean square of the electric field, and
a value of the $k(\omega)$ is determined according to a relative permittivity $\varepsilon^*_p$ of the particle and a relative permittivity $\varepsilon^*_m$ of the medium as in Equation 2:

$$K(\omega) = \frac{\varepsilon^*_p - \varepsilon^*_m}{\varepsilon^*_p + 2\varepsilon^*_m} \qquad \text{[Equation 2]}$$

wherein a magnitude and direction of dielectrophoresis induced to each particle that constitutes the target biomaterials changes depending on voltage and frequency of the electric field and dielectric properties of the particle and the medium including conductivity σ and permittivity ε, to generate a negative dielectrophoretic force having the $k(\omega)$ value of less than 0;
wherein a Calixcrown Self-Assembled Monolayer (SAM) or a polyvinylpyrrolidone surface modified material layer is further formed as a linking molecule layer on a surface of the insulating layer between the first and second interdigitated microelectrodes to selectively immobilize beta-amyloid antibodies, and
wherein the plurality of receptors includes at least one of beta-amyloid antibodies, aptamers and peptides, and is immobilized on an upper surface of the insulating layer exposed to the space between the first interdigitated microelectrode and the second interdigitated microelectrode;
the interdigitated electrode biosensor further comprising
   a protective cap configured to fully cover the first interdigitated microelectrode and the second interdigitated microelectrode including the insulating layer,
   a polydimethylsiloxane (PDMS) chip having two microchannels, wherein the PDMS chip is attached to prevent non-specific binding of a material other than beta-amyloid, and
   an adsorption blocking layer (Bovine Serum Albumin) coated on an inner wall of the protective cap except a region where the plurality of receptors is immobilized and a surface of the first and second interdigitated microelectrodes, and
wherein the protective cap comprises
   a first side portion extending along an outer edge of the first interdigitated microelectrode, a first portion of the adsorption blocking layer extending from an upper surface of the insulating layer along an inner surface of the first side portion and being interposed between the inner surface of the first side portion and the outer edge of the first interdigitated microelectrode,
   a second side portion extending along an outer edge of the second interdigitated microelectrode, a second portion of the adsorption blocking layer extending from the upper surface of the insulating layer along an inner surface of the second side portion and being interposed between the inner surface of the second side portion and the outer edge of the second interdigitated microelectrode, and
   an upper portion extending between and connecting the first side portion and the second side portion, a third portion of the adsorption blocking layer extending along a lower surface of the upper portion and along inner surfaces, respectively, of the first side portion and the second side portion.

2. The interdigitated electrode biosensor using dielectrophoresis according to claim 1, wherein an operating frequency of the interdigitated electrode biosensor is 10 Hz-100 Hz.

3. The interdigitated electrode biosensor using dielectrophoresis according to claim 2, wherein a spacing between the first interdigitated microelectrode and the second interdigitated microelectrode is 3-7 μm.

* * * * *